United States Patent [19]  [11]  4,359,405
Mount et al.  [45]  Nov. 16, 1982

[54] SOLVENT CONDITIONING OF PHOSPHORUS-VANADIUM-OXYGEN CATALYSTS

[75] Inventors: Ramon A. Mount; Warn D. Robinson, both of St. Louis, Mo.

[73] Assignee: Monsanto Company, St. Louis, Mo.

[21] Appl. No.: 218,603

[22] Filed: Dec. 22, 1980

[51] Int. Cl.³ .............................................. B01J 27/14
[52] U.S. Cl. ...................................... 252/435; 252/437
[58] Field of Search ................................ 252/435, 437

[56] References Cited

U.S. PATENT DOCUMENTS

| | | | |
|---|---|---|---|
| 3,293,268 | 12/1966 | Bergman | 260/346.8 |
| 3,985,775 | 8/1976 | Harrison | 252/437 X |
| 4,043,943 | 8/1977 | Schneider | 252/435 X |
| 4,062,873 | 12/1977 | Harrison | 252/437 X |
| 4,080,312 | 3/1978 | Farha, Jr. et al. | 252/435 X |
| 4,092,269 | 5/1978 | Mount et al. | 252/437 X |
| 4,244,879 | 1/1981 | Bremer et al. | 252/437 X |
| 4,283,307 | 8/1981 | Barone et al. | 252/437 X |
| 4,294,722 | 10/1981 | Bremer et al. | 252/437 X |

OTHER PUBLICATIONS

Chemical Engineer's Handbook 4th Ed. Perry, McGraw Hill New York, (8–59)–(8–61).

Primary Examiner—Delbert E. Gantz
Assistant Examiner—William G. Wright
Attorney, Agent, or Firm—Thomas Y. Awalt, Jr.

[57] ABSTRACT

In the preparation of phosphorus-vanadium-oxygen catalyst, where vanadium and phosphorus are contacted under conditions to provide a catalyst precursor with vanadium in the tetravalent state, and the precursor is formed into agglomerations and subsequently calcined at high temperatures, the improvement which comprises contacting the catalyst precursor with a non-aqueous solvent in an amount sufficient to enhance crush strength.

31 Claims, No Drawings

SOLVENT CONDITIONING OF PHOSPHORUS-VANADIUM-OXYGEN CATALYSTS

BACKGROUND OF THE INVENTION

1. Field of the Invention

The invention relates to a method for preparing catalysts useful in the manufacture of maleic anhydride by the oxidation of aliphatic hydrocarbons, and more particularly to low attrition catalysts suitable for producing maleic anhydride from saturated hydrocarbons in high yields.

2. Description of the Prior Art

Bergman et al., U.S. Pat. No. 3,293,268 (hereby incorporated by reference) teaches a process of oxidizing saturated aliphatic hydrocarbons to produce maleic anhydride under controlled conditions in the presence of a phosphorus-vanadium-oxygen catalyst.

Typical phosphorus-vanadium-oxygen catalysts for use in tube-type reactors are formed as pills, pellets, slugs, tablets, or extrusions, collectively termed "agglomerates". Charging of such catalyst agglomerates to a reactor is a problem because the agglomerates are dusty, that is, have very low breakage and attrition resistance, and the phosphorus-vanadium-oxygen dust is moderately toxic. When catalyst structures are broken the breakage can cause undesirable pressure drop difficulties during reactor operation. In attempts to alleviate such problems, high density forms have been employed using higher tabletting pressures. These high density forms, with corresponding lower porosity, are less active than low density forms.

If the crush strength of low density phosphorus-vanadium-oxygen catalysts could be significantly improved without detriment to catalyst performance such improvement would constitute a significant advance in the art and is an object of this invention.

SUMMARY OF THE INVENTION

These and other advantages are achieved in a process for preparing phosphorus-vanadium-oxygen complex catalysts by contacting vanadium and phosphorus under conditions to provide a catalyst precursor having greater than 50 atom % tetravalent vanadium, recovering the precursor, forming the catalyst into agglomerates and calcining the catalyst precursors by the improvement comprising contacting the catalyst precursor with a nonaqueous solvent in an amount sufficient to increase crush strength prior to calcining and then drying the catalyst precursor. Contacting with solvent may take place before the formation of the catalyst precursor into agglomerates, after the formation of the catalyst precursor into agglomerates, or both before and after.

DEFINITIONS

As used herein the term "agglomeration" means the gathering together of particulates, particularly powdered materials which are brought together in a loose state of bonding to form larger particulates or structures. Such "agglomerates" are usually redispersible.

The terms "granules" and "nodules" describe forms of agglomerates by reference to the end-condition of the product. "Granulation" and "granules" are used to describe the formation of particulates, and the resultant irregularly shaped clusters. "Nodulizing" and "nodules" are used to describe the formation of, and the resultant generally regularly shaped clusters, of particulates, such as pills and pellets.

By "non-aqueous solvent" is meant any solvent not containing a substantial amount of water. A "substantial" amount is an amount over and above the amount ordinarily found as impurities in commercial lots. The solvent and any other constituents should, of course, be relatively inert to the catalyst precursor. Preferably the solvent is an organic solvent selected from the group consisting of benzene and derivatives of benzene ketones, nitriles, esters, alcohols and halogenated hydrocarbons. Used properly, these solvents result in reduced attrition as well as increased crush strength.

The term "attrition" means degrading or deagglomerizing by wearing or grinding down through friction or breakage of the catalyst agglomerates or structures into dusts and/or fines.

The term "percent (or %) attrition" means, according to the test described below, the weight loss in grams by friction and breakage of the catalyst structures (initial weight, grams—subsequent weight, grams) divided by the initial weight in grams of the catalyst structures, the quotient having been multiplied by 100.

"Average crush strength" means, the average of 10 or more crush strength tests according to the test described below, in terms of pounds of force.

The term "yield" means the ratio of the moles of maleic anhydride obtained to the moles of feed material introduced into the reactor.

The term "space velocity" means the hourly volume of gaseous feed expressed in cubic centimeters (cc) at 15.5° C. at standard atmospheric pressure, divided by the catalyst bulk volume, expressed in cubic centimeters, the term expressed as cc/cc/hour.

Except as otherwise indicated the term "catalyst precursor" is used herein includes the catalyst after calcining but before the conditioning.

DETAILED DESCRIPTION OF THE INVENTION

Broadly described, the catalysts of this invention are prepared by contacting a phosphorus compound and a vanadium compound under conditions which will provide a catalyst precursor having a phosphorus to vanadium atom ratio between about 1:2 and about 2:1, and having greater than 50 atom percent of the vanadium in the tetravalent state. The catalyst precursors are recovered and formed into structures for use in a maleic anhydride reactor. Thereafter, these catalyst precursors are calcined at a temperature between about 300° C. and about 600° C. to form the catalyst.

The vanadium compounds useful as a source of vanadium in the catalyst precursors are well known in the art. Suitable vanadium compounds include but are not limited to: vanadium oxides, such as vanadium pentoxide, vanadium tetroxide, vanadium trioxide, and the like, vanadium oxyhalides, such as vanadyl chloride, vanadyl dichloride, vanadyl trichloride, vanadyl bromide, vanadyl dibromide, vanadyl tribromide and the like; vanadium-containing acids, such as metavanadic acid, pyrovanadic acid, and the like; vanadium salts, such as ammonium metavanadate, vanadium sulfate, vanadium phosphate, vanadyl formate, vanadyl oxylate, and the like. Of these, however, vanadium pentoxide is preferred.

The compounds useful as a source of phosphorus in the catalyst precursors are also well known to the art. Suitable phosphorus compounds include: phosphoric acids, such as orthophosphoric acid, metaphosphoric acid, and the like; phosphorus oxides, such as, phosphorus pentoxide and the like; phosphorus halides, such as phosphorus pentachloride, phosphorus oxybromide, phosphorus oxychloride, and the like; trivalent phosphorus compounds, such as phosphorous acid, phosphorus trihalides (for example, phosphorus trichloride), organic phosphites (for example, trimethyl phosphite), sometimes known as phosphonates, and the like. Of these, orthophosphoric acid and phosphorus pentoxide are preferred, with a mixture of orthophosphoric acid and phosphorous acid being most preferred.

Preparation of Catalyst Precursors

To prepare the catalyst precursors by the process of the present invention, a vanadium compound is brought together with a phosphorus compound in an acid solution and the mixture is heated to dissolve the starting materials. A reducing agent is used to reduce pentavalent vanadium to tetravalent vanadium and to maintain the vanadium in the tetravalent state. As is well known to those skilled in the art, hydrogen halide acid or oxalic acid solutions, which are mild reducing agents, can serve not only as the acid but also as the reducing agent for the pentavalent vanadium. On the other hand, a trivalent phosphorus compound can be used to provide tetravalent vanadium and also serve as a source of phosphorus to provide the catalyst precursor. It is preferred to use phosphorus acid as the trivalent phosphorus compound which serves as an acid medium to provide the tetravalent vanadium in the precursor. The acid solution containing the phosphorus compound and the vanadium compound is heated until a blue solution is obtained, indicating that at least 50 atom percent of the vanadium is in the tetravalent state. The amount of time required to dissolve the phosphorus compound and the vanadium compound and to provide a substantial amount of the vanadium in the tetravalent state and to provide the catalyst precursors varies from batch to batch, depending upon the compounds used as starting materials and the temperature at which the compounds are heated. In general, however, heating the solution to at least 100° C. for about 4 hours is sufficient.

The atom ratio of phosphorus to vanadium in the starting materials is important since it controls the phosphorus to vanadium atom ratio in the final catalyst. When phosphorus-vanadium-oxygen precursors contain a phosphorus to vanadium atom ratio below about 0.5:1 or above about 2:1, the yield of maleic anhydride using the catalyst prepared from these precursors is so low that it is not of commercial significance. It is preferred that phosphorus-vanadium-oxygen precursors have a phosphorus to vanadium atom ratio between about 1:1 and about 1.5:1. When the catalyst is used to convert a feed that is primarily butane to maleic anhydride, it is even more preferable that the precursor have a phosphorus to vanadium atom ratio between about 1:1 and about 1.2:1.

If desired, although not actually required, a nonionic surfactant may be added to the mixture to control particle size and prevent agglomeration of the catalyst precursor during the preparation step. Nonionic surfactants may be broadly defined as compounds, aliphatic or alkyl-aromatic in nature, which do not ionize in water solution. For example, a well known class of nonionic surfactants is made available on the market under the trade name of "Pluronic". These compounds are formed by condensing ethylene oxide with a hydrophobic base formed by the condensation of propylene oxide with propylene glycol. The hydrophobic portion of the molecule which, of course, exhibits water insolubility, has a molecular weight of from about 1,500 to 1,800. The addition of polyoxyethylene radicals to this hydrophobic portion tends to increase the water solubility of the molecule as a whole and the liquid character of the product is retained up to the point where polyoxyethylene content is about 50% of the total weight of the condensation product. Other suitable surfactants are described in U.S. Pat. No. 4,149,992.

The amount of surfactant, when employed, suitable for use in the process of the present invention, can vary within wide limits. It has been found that the amount of surfactant should be at least about 0.1% by weight, based on the total weight of the mixture or dispersion, since at lower concentrations the effect of the surfactant is diminished considerably. On the other hand, there is no upper limit as to the amount of surfactant that can be used, although there does not seem to be any advantage in using more than about 1.0% by weight, and usually between about 0.05% and about 0.5% by weight, based on the total weight of the dispersion.

Recovery of the Catalyst Precursor

After the vanadium and phosphorus compounds are contacted and a substantial amount of the vanadium is in the tetravalent state, it is necessary to recover the phosphorus-vanadium-oxygen catalyst precursors. Techniques for recovering the catalyst precursors are well known to those skilled in the art. For example, the catalyst precursors can be deposited from aqueous solution on a carrier, such as alumina or titania, or alternatively, the catalyst precursors can be recovered by gentle heating to dryness to provide solid phosphorus-vanadium-oxygen catalyst precursors. This latter technique is preferred.

Forming Agglomerates

After the phosphorus-vanadium-oxygen catalyst precursors have been recovered as dry powders, they are formed into agglomerates or structures, prior to subjecting them to calcining conditions.

Techniques for forming appropriate agglomerates from precursors for use in a fluidized bed reactor or in a fixed-tube heat-exchanger type reactor are well known to those skilled in the art. For example, the precursor can be deposited on a carrier or comminuted for use in a fluidized bed reactor, or structured for use in fixed-tube heat exchanger-type reactors by prilling, tabletting, pelletizing or granulating the precursors by conventional means.

Contacting with Solvent and Drying the Catalyst Precursor

The contacting with solvent may take place before or after the forming of the agglomerates, or both before and after the forming of the agglomerates, and preferably before calcining. The non-aqueous solvent is applied to the catalyst precursor by spray, fog, sprinkle, or immersion. The manner of application will ordinarily be selected on the basis of the characteristics of the particular solvent with due regard for its abundance and cost. The amount of solvent applied is not critical so far as crush strength is concerned because any amount will to some extent enhance crush strength. However in the case of certain solvents such as ethyl acetate, the amount of solvent applied and/or method of application may control the amount of attrition. We have discovered that spraying, for example, with ethyl acetate will cause a slight increase in calcined attrition; soaking the same solvent will decrease calcined attrition.

It is not unknown to use liquids in the formation or the holding of agglomerates, the theory being that the liquid acts as a binder between particles, minute portions of the outer perimeters of which are dissolved and then solidified on drying. What is unique about this invention is that the solvent application can be made to a phosphorus-vanadium-oxygen catalyst precursor, without interfering in any way with subsequent catalyst activity, to achieve higher crush strength preferably in combination with low attrition not only in handling of the catalyst, but in the use of the catalyst as well. After contacting with solvent and preferably before calcining the solvent should be removed in a conventional drying step at temperatures of 70°–250° C. (100°–150° C. preferred).

The precursors are then calcined at temperatures between about 300° and about 600° C. for at least two hours to provide the catalysts of the present invention. It is preferred to convert part of the tetravalent vanadium to pentavalent vanadium during the calcination step. The tetravalent vanadium can be converted to pentavalent vanadium by calcining the precursor in a free oxygen-containing gas, such as air, at temperatures of about 300° to about 600° C. until about 20 to about 90 atom percent of the vanadium has been converted to pentavalent vanadium. If more than about 90 atom percent of the vanadium is converted to pentavalent vanadium, usually caused by calcining too long or at too high a temperature, the selectivity of the resultant catalyst, and consequently, the yield of maleic anhydride decrease. On the other hand, conversion of less than about 20 atom percent of the vanadium during air calcination does not seem to be beneficial. As will occur to those skilled in the art, the exact calcination conditions will depend on the method of preparing the precursor, equipment configurations, or additives to the precursor; however, it has been found that calcination at 400°–500° C. for about 4 hours is generally sufficient.

After calcining, the catalyst precursors can be charged to a suitable reactor without suffering the breakage difficulties usually associated with prior art phosphorus-vanadium-oxygen catalyst and in some cases with substantially less attrition and can be used in accordance with prior art techniques to convert non-aromatic hydrocarbons to maleic anhydride.

Preparation of Maleic Anhydride

The catalysts of the present invention are useful in a variety of reactors to convert non-aromatic hydrocarbons to maleic anhydride. Both fluidized bed reactors and fixed tube, heat exchanger type reactors are satisfactory, and the details of the operation of such reactors are well known to those skilled in the art. The reaction to convert non-aromatic hydrocarbons to maleic anhydride requires only contacting the hydrocarbons admixed with a free-oxygen containing gas, such as air or oxygen enriched air, with the catalysts at elevated temperatures. The hydrocarbon/air mixture is contacted with the catalyst at a concentration of about 1 mole percent to about 10 mole percent hydrocarbon at a space velocity of about 100 cc/cc/hour to about 3,000 cc/cc/hour at temperatures between about 300° C. and about 600° C. to provide excellent yields of maleic anhydride. Maleic anhydride produced by using the conditioned catalysts of this invention can be recovered by any number manner well known to those skilled in the art. For example, maleic anhydride can be recovered by direct condensation or by absorption in suitable media with subsequent separation and purification of the anhydride.

A large number of non-aromatic hydrocarbons having from 4 to 10 carbon atoms can be converted to maleic anhydride using the catalysts prepared according to the present process. It is only necessary that the hydrocarbon contain not less than 4 carbon atoms in a straight chain. As an example, the saturated hydrocarbon n-butane is satisfactory, but isobutane (2-methylpropane) is not satisfactory for conversion to maleic anhydride although its presence is not harmful. In addition to n-butane, other suitable saturated hydrocarbons include the pentanes, the hexanes, the heptanes, the octanes, the nonanes, the decanes, and mixtures of any of these, with or without n-butane.

Unsaturated hydrocarbons are also suitable for conversion to maleic anhydride using the agglomerated catalysts of this invention. Suitable unsaturated hydrocarbons include the butenes (1-butene and 2-butene), 1,3-butadiene, the pentenes, the hexenes, the heptenes, the octenes, the nonenes, the decenes and mixtures of any of these, with or without the butenes.

Cyclic compounds such as cyclopentane, cyclopentene, oxygenated compounds such as furan, dihydrofuran, or even tetrahydrofurfural are also satisfactory.

Of the aforementioned feedstocks, n-butane is the preferred saturated hydrocarbon and the butenes are the preferred unsaturated hydrocarbons, with n-butane being most preferred of all feedstocks.

It will be noted that the aforementioned feedstocks need not necessarily be pure substances, but can be technical grade hydrocarbons.

The principal product from the oxidation of the above feed materials is maleic anhydride, although small amounts of citraconic anhydride (methylmaleic anhydride) may also be produced when the feedstock is a hydrocarbon containing more than 4 carbon atoms.

The following examples illustrate the invention, but should not be construed as delimiting.

Catalyst Precursor Preparation

To a mixture of 340.0 grams (1.87 moles) of vanadium pentoxide, 1150 milliliters of water and 2.3 grams of Sterox ® NJ nonionic surfactant were added 228.0 grams (1.98 moles) of 85% orthophosphoric acid and 173.0 grams (2.06 mole) of 97.6% phosphorous acid. The phosphorus to vanadium atom ratio was about 1.08:1. The aqueous mixture of vanadium and phosphorus compounds was charged to a 2-liter Parr autoclave, fitted with a thermowell, two 6-bladed stirrers, and a vent, and heated to about 100° C. and thereafter sealed. The mixture, while being stirred at 1,000 revolutions per minute (rpm), was heated to about 150° C. in about 50±10 minutes and held at this temperature for about 4 hours. After the hold period, the autoclave was cooled to about 80° C. in 50±10 minutes and opened. The aqueous phosphorus-vanadium-oxygen catalyst precursor slurry was placed in an open dish casserole or tray and evaporated to dryness in an oven at about 120° C. The resultant phosphorus-vanadium-oxygen catalyst precursor powder was ground to pass an 18 mesh sieve (U.S. Standard Sieve Size), and formed into 3/16 inch diameter tablets using one weight percent graphite as the tabletting lubricant.

Crush Strength Test

This procedure illustrates the crush strength test used to determine the average crush strength (measured as longitudinal, side crush strength for tablets) of the phosphorus-vanadium-oxygen catalyst precursor structures.

A John Chatillon and Sons Universal Test Stand, Model LTCM (motorized, variable speed unit equipped with Chatillon Dial Push/Pull Gauges, either Model DPP-10 (10 pounds maximum) or Model DPP-50 (50 pounds maximum), depending on the anticipated range of crush strength, was used as the test equipment.

The tablet was placed on its side under the center of the plunger and the instrument driven in the automatic mode at a setting of 2. The maximum force exerted during the test was taken as the crush strength for the tablet. Generally 10 or more determinations were made from a given sample of tablets and the crush strength values averaged to give an average crush strength (ACS). The results are reported in Table 1.

Attrition Test

This procedure illustrates the attrition test used to determine percent attrition of the phosphorus-vanadium-oxygen catalyst precursors (or catalysts).

A 17.78 centimeter (7.0 inch) high ×9.525 centimeter (3.75 inch) outside diameter 0.946 liter (1.0 quart) jar equipped with a screw-on cap and two 1.27 centimeter (0.5 inch) high×8.89 centimeter (3.5 inch) long stainless steel baffles cemented lengthwise to the inner sides at 180° opposed angles was employed.

The catalyst samples were separately screened, using a 10 mesh sieve (U.S. Standard Sieve Size) to remove any dust and fines. Approximately 50.00 grams of each of the screened samples were accurately weighed (initial weight in grams) and charged to the apparatus described above. The baffled jar containing the catalyst precursor was placed on a roller mill and rolled at 160±5 revolutions per minute (rpm) for 15 minutes. The sample was then removed from the jar, screened, and weighed (subsequent weight in grams) to determine the amount of attrited material which passed through the 10 mesh sieve. The percent attrition was calculated as follows:

% Attrition =

$$\frac{\text{Initial weight, grams} - \text{Subsequent weight, grams}}{\text{Initial weight, grams}} \times 100$$

The results are shown in Table 1 under the columns headed "% Attrition".

Catalyst Testing

The catalysts were tested by placing the calcined pellets in fixed tube reactors of about 0.8" diameter, 6" length. The catalysts were conditioned for at least 16 hours using a feed stream containing 1.5 mole percent butane in air; space velocity was about 1450 cc/cc/hr.

Comparisons were made between treated and untreated catalyts to insure strengthened pellets exhibited performance as good as baseline catalyst. Performance test conditions used for the comparisons included $1.5\%/1450 \text{ hr}^{-1}$.

EXAMPLES 1-12

Except with respect to Example 12 which was soaked for 5 minutes in ethyl acetate, the catalyst precursor tablets were placed in a tray and quantities of the designated solvent atomized or misted over the structure while being gently rolled so that all sides of the structures would be exposed to the solvent. The solvent was removed by placing the structures in a forced draft oven at room temperature (23° C.). The temperature of the oven was increased over a period of about one hour to about 125° C. and maintained at about 125° C. for 2-4 hours. Thereafter, the hardened structures were calcined at 400°-500° C. for about four hours to convert the catalyst precursor to active catalyst.

Samples of both uncalcined (after solvent removed) and calcined structures were subjected to the crush strength and attrition tests to determine the effect of type and amount of solvent on the hardening or strengthening of the structures as a result of the treatment. The results are shown in Table 1.

TABLE 1

PELLET STRENGTHENING BY TREATMENT WITH NON-AQUEOUS SOLVENTS

| Example | Solvent (% Used) | Uncalcined % Attrition | Uncalcined ACS, lb. | Calcined % Attrition | Calcined ACS, lb. | % Loss on Drying | % Loss on Calcining |
|---|---|---|---|---|---|---|---|
| 1* | None (control) | 7.0 | 2.08 | 2.6 | 8.03 | — | — |
| 2 | Toluene (3%) | 5.3 | 3.01 | 2.4 | 9.14 | 0.4 | 7.9 |
| 3 | Methyl Ethyl Ketone (3.12%) | 3.8 | 2.67 | 2.4 | 9.67 | 0.0 | 8.2 |
| 4 | Cyclohexanone (6.08%) | 8.3 | 3.33 | 3.4 | 10.36 | 0.4 | 8.2 |
| 5 | Acetonitrile (10.4%) | 6.0 | 3.24 | 3.3 | 10.62 | 0.3 | 8.3 |
| 6 | Ethyl Acetate (10.5%)[1] | 6.9 | 4.86 | 4.0 | 9.18 | 0.7 | 8.0 |
| 7 | Methylene Chloride (21.8%)[1] | 8.1 | 4.19 | 3.0 | 10.83 | 0.7 | 7.7 |
| 8 | Ethylene Glycol (9.0%) | 6.4 | 5.42 | 3.2 | 9.96 | (0.03 gain) | 8.2 |
| 9 | Diglyme[2] (9.4%)[1] | 9.8 | 4.57 | 2.9 | 10.73 | 0.7 | 8.9 |
| 10* | None (control) | | | | 8.61 | — | 8.2 |
| 11 | Methyl Ethyl Ketone (15%)[1] | | | | 8.78 | 0.4 | 9.4 |
| 12 | Ethyl Acetate (Soak) | 3.8 | 2.81 | 1.8 | 9.85 | 2. | 8.6 |
| 13* | None (control) | 15.6 | 8.3 | 8.9 | 20.9 | 0.9 | 8.0 |
| 14 | Toluene (soak) | 14.4 | 13.99 | 7.6 | 25.88 | 1.7 | 9.6 |
| 15 | Acetonitrile (soak) | 15.3 | 10.97 | 8.5 | 18.19 | 3.8 | 6.8 |
| 16 | Ethylene Glycol (soak) | 10.6 | 4.78 | 10.9 | 9.44 | 26 | 9.8 |

[1]This amount was sprayed from a weighed atomizer. The amount of solvent actually sorbed onto the catalyst was undetermined.
[2]Bis-(2-methoxyethyl) ether
*comparative (for examples to follow)

EXAMPLES 17 and 18

The catalysts of Examples 10 and 11 were tested for performance in the preparation of maleic anhydride from butane as explained above under "Catalyst Testing", with results as shown in the following table.

TABLE 2

PERFORMANCE TESTS — NON-AQUEOUS SOLVENT TREATMENT

| | | Test Conditions | | | | Test Results | |
|---|---|---|---|---|---|---|---|
| Example | Solvent | Bath Temp. | Feed Conc. | Space Velocity | Test Hours | % Butane Conversion | Mole % MAN Yield |
| 17* | None (control) | 408° C. | 1.5% | 1433 hr$^{-1}$ | 159 | 80.3 | 52.6 |
| 18 | Methyl Ethyl Ketone | 408 | 1.5 | 1430 | 160 | 78.7 | 51.6 |

*comparative

We claim:

1. In a process for preparing phosphorus-vanadium-oxygen complex catalysts having a phosphorus to vanadium atom ratio in the range of about 1:2 to about 2:1, the process comprising:
   (a) contacting vanadium and phosphorus compounds under conditions which will provide a catalyst precursor wherein greater than 50 atom % of the vanadium is in the tetravalent state;
   (b) recovering the catalyst precursor in a dry condition;
   (c) forming the catalyst precursor into agglomerates; and
   (d) calcining the catalyst precursor agglomerations at a temperature between about 300° C. and 600° C., the improvement comprising contacting the recovered dry catalyst precursor with a non-aqueous solvent in an amount sufficient to increase crush strength and then drying the catalyst precursor.

2. The process improvement of claim 1 wherein the non-aqueous solvent is selected from the group consisting of benzene and derivatives of benzene, ketones, nitriles, esters, alcohols and halogenated hydrocarbons.

3. The process of claim 1 wherein the nonaqueous solvent is a benzene derivative.

4. The process improvement of claim 3 wherein the non-aqueous solvent is toluene.

5. The process improvement of claim 1 wherein the non-aqueous solvent is a ketone.

6. The process improvement of claim 5 wherein the ketone is methyl ethyl ketone.

7. The process improvement of claim 5 wherein the ketone is cyclohexanone.

8. The process improvement of claim 1 wherein the non-aqueous solvent is a nitrile.

9. The process improvement of claim 8 wherein the nitrile is acetonitrile.

10. The process improvement of claim 1 wherein the non-aqueous solvent is an ester.

11. The process improvement of claim 10 wherein the ester is ethyl acetate.

12. The process improvement of claim 1 wherein the non-aqueous solvent is a halogenated hydrocarbon.

13. The process improvement of claim 12 wherein the halogenated hydrocarbons is methylene chloride.

14. The process improvement of claim 1 wherein the non-aqueous solvent is an alcohol.

15. The process improvement of claim 14 wherein the alcohol is ethylene glycol.

16. The process improvement of claim 1 wherein contacting is by spraying.

17. The process improvement of claim 1 wherein contacting is by soaking.

18. The process improvement of claim 1 wherein the catalyst precursor is contacted with solvent after being formed into agglomerates.

19. The process improvement of claim 1 wherein the catalyst precursor is contacted with the solvent before the catalyst precursor is formed into agglomerates.

20. The process improvement of claim 1 wherein the catalyst precursor is contacted with solvent before and after being formed into agglomerates.

21. The process improvement of claim 1 wherein the agglomerates are granules.

22. The process improvement of claim 1 wherein the agglomerates are broken slugs.

23. The process improvement of claim 1 wherein the agglomerates are nodules.

24. The process improvement of claim 1 wherein the agglomerates are tablets.

25. The process improvement of claim 1 wherein the agglomerates are pills.

26. The process improvement of claim 1 wherein a surfactant is employed in the preparation of the catalyst precursor.

27. The process improvement of claim 1 wherein drying is accomplished at a temperature of 70°-250° C.

28. The process improvement of claim 1 wherein drying is accomplished at a temperature of 100°-150° C.

29. The process improvement of claim 1 wherein drying is accomplished at a temperature of about 125° C.

30. A phosphorus-vanadium-oxygen catalyst prepared by the improved process of claim 1.

31. The catalyst of claim 30 having a crush strength of at least about 9 and a % attrition less than about 2%.

* * * * *